United States Patent
Brandt et al.

(10) Patent No.: US 10,172,737 B2
(45) Date of Patent: Jan. 8, 2019

(54) SOUND REDUCING OSTOMY BAG

(71) Applicants: Joergen-Ulrik Brandt, Bogense (DK); Tina Joergensen, Bogense (DK)

(72) Inventors: Joergen-Ulrik Brandt, Bogense (DK); Tina Joergensen, Bogense (DK)

(*) Notice: Subject to any disclaimer, the term of this patent is extended or adjusted under 35 U.S.C. 154(b) by 348 days.

(21) Appl. No.: 15/123,174

(22) PCT Filed: Feb. 26, 2015

(86) PCT No.: PCT/DK2015/050039
§ 371 (c)(1),
(2) Date: Sep. 1, 2016

(87) PCT Pub. No.: WO2015/131905
PCT Pub. Date: Sep. 11, 2015

(65) Prior Publication Data
US 2017/0065451 A1  Mar. 9, 2017

(30) Foreign Application Priority Data
Mar. 4, 2014 (DK) ................... 2014 70105

(51) Int. Cl.
*A61F 5/441* (2006.01)
*A61F 5/445* (2006.01)

(52) U.S. Cl.
CPC ............ *A61F 5/441* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,406,657 A | * | 9/1983 | Curutcharry | A61F 5/441 604/328 |
| 6,050,983 A | * | 4/2000 | Moore | A61F 5/4405 128/DIG. 24 |
| 6,709,421 B1 | * | 3/2004 | Falconer | A61F 5/441 604/335 |
| 7,160,275 B2 | * | 1/2007 | Falconer | A61F 5/441 604/333 |
| 7,270,860 B2 | * | 9/2007 | Giori | A61F 5/445 428/35.7 |
| 8,221,368 B2 | * | 7/2012 | Forbes | A61F 5/445 600/32 |

(Continued)

FOREIGN PATENT DOCUMENTS

| | | |
|---|---|---|
| DE | 3639171 A1 | 5/1988 |
| GB | 2481893 A | 1/2012 |

OTHER PUBLICATIONS

International Search Report and Written Opinion from International Patent Application No. PCT/DK2015/050039, dated May 13, 2015.

*Primary Examiner* — Tatyana Zalukaeva
*Assistant Examiner* — Guy K Townsend
(74) *Attorney, Agent, or Firm* — Merchant & Gould P.C.

(57) ABSTRACT

There is provided an ostomy bag assembly with sound reducing means composed of a proximal membrane and a distal membrane in immediate contact and with misaligned apertures that blocks the passage from the stoma to the lumen of the ostomy bag unless the membranes are expanded due to the pressure difference established when flatus gases escape the stoma.

10 Claims, 2 Drawing Sheets

(56) References Cited

U.S. PATENT DOCUMENTS

| | | | |
|---|---|---|---|
| 8,316,985 B2* | 11/2012 | Bain | A61F 5/441 |
| | | | 181/198 |
| 2005/0015065 A1* | 1/2005 | Falconer | A61F 5/441 |
| | | | 604/335 |
| 2005/0112338 A1* | 5/2005 | Faulks | A61F 13/51405 |
| | | | 428/204 |
| 2008/0294129 A1* | 11/2008 | Giori | A61F 5/445 |
| | | | 604/332 |
| 2011/0147114 A1* | 6/2011 | Bain | A61F 5/4404 |
| | | | 181/198 |
| 2011/0218451 A1* | 9/2011 | Lai | A61F 5/56 |
| | | | 600/533 |
| 2012/0010580 A1* | 1/2012 | Forbes | A61F 5/441 |
| | | | 604/339 |
| 2013/0019374 A1* | 1/2013 | Schwartz | A61F 5/00 |
| | | | 2/69 |
| 2016/0114974 A1* | 4/2016 | Kurihara | B32B 27/32 |
| | | | 383/71 |
| 2016/0228283 A1* | 8/2016 | Patchett | A61L 28/0003 |
| 2017/0065451 A1* | 3/2017 | Brandt | A61F 5/445 |

* cited by examiner

SOUND REDUCING OSTOMY BAG

CROSS-REFERENCE TO RELATED APPLICATIONS

This application is a National Stage Application of International Patent Application No. PCT/DK2015/050039, filed 26 Feb. 2015, which claims benefit of Serial No. PA 2014 70105, filed 4 Mar. 2014 in Denmark and which application(s) are incorporated herein by reference. To the extent appropriate, a claim of priority is made to each of the above disclosed applications.

FIELD OF THE INVENTION

The present invention relates to a disposable ostomy bag assembly with a bag for receiving bodily waste materials. More specifically the present invention relates to an ostomy bag assembly provided with sound reducing means.

BACKGROUND OF THE INVENTION

Following surgery, patients who have had a surgical construction of an artificial excretory opening such as ileostomy or colostomy patients use ileostomy/colostomy bags (collectively referred to as ostomy bags) to collect bodily waste materials. These bodily waste materials include gases, liquids and solids. The waste material may be semi-solid faecal waste. It is desirable in any event to dispose the collected materials with minimal handling from the user. It is also desirable to avoid undesired smell to escape from the ostomy bag when it is detached from the patient after use and before being disposed.

Some bags are intended for multiple use purposes and generally the surgical patients find that they have to empty the collection bag many times during the day. A given collection bag is thus fitted with waste discharge outlet through which the waste materials collected from the artificial excretory opening can be discharged. It is not unusual to empty these bags between six and ten times in any given day. A collection bag will typically be worn for a number of consecutive days before being replaced with a new bag. Given the nature of the materials which they collect, such collection bags are generally made of plastics materials.

Once the stoma is in place, however, gas created by the digestion of food builds up behind the stoma and when the pressure is too great for the stoma opening to prevent its release, the gas escapes through the stoma in a sequential series of closely linked gas bubbles, causing the stoma to rapidly open and close. The rapid opening and closing of the stoma creates an audible noise. This flatulence can become a problem as the user has no way of controlling the escape of gas from the stoma or the noise associated with this. Additionally, the noise can often cause embarrassment to a person having a colostomy.

While there have been developments in managing other challenges such as odor discharging from a stoma, little has been effectively done to control noise emanating from the stoma. One sound abatement device that has been developed comprises a woven pouch configured to receive a stoma bag. However, the pouch requires the use of additional hardware, such as a belt or otherwise, to maintain the position of the bag. Unfortunately, the use of additional hardware can be noticeable and uncomfortable as the material of the hardware is typically kept under pressure. During the day, it is difficult for an individual to obtain reprieve from irritation caused by the additional hardware and must wait until he or she is in private, such as at home, to remove the hardware. This is because, often, the device is bulky and wrapped entirely about the individual and disposed under clothing. Further, some bags used for sound abatement is formed of woven material, which is less than satisfactory for the reduction of noise.

U.S. Pat. No. 4,406,657 describes a method for reducing the noise resulting from flatulence. It describes an oblong device made of porous material which is inserted into the colon using the stoma. The device has a hole which acts to keep the stoma open so that gases can pass through the device and the stoma without any pressure build-up and consequent noise production. However, whenever a stool is passed the device is pushed out of the stoma and into the colostomy bag. This results in a number of disadvantages, for example, after a stool has been passed the device is no longer in the stoma and therefore, the patient is susceptible to gas build up and consequent noises discussed above. Alternatively, it is suggested that the device ejected into the bag can be reinserted by hand into the end portion of the intestine; however, this may not always be convenient.

US2011147114 describes means for the abatement of noise emanating from surgically created abdominal stomas. The sound abatement means includes a noise suppressor formed of sound dampening material, which defines an opening and cavity suitable in size and shape for receiving and enveloping a stoma formed through a body wall of an individual.

Improved means for reducing the disturbance caused by the noise when gas exits the stoma is needed.

SUMMARY OF THE INVENTION

The present invention solves the known problems associated with stoma noise by providing a novel sound reducing means. Thus, the present invention provides an ostomy bag assembly (1) with sound reducing means comprising:
- a bag (2) for receiving bodily waste materials through an opening;
- a sound reducing device (3) positioned in the opening of the bag; and
- a flange (4) for securing the assembly to the body of a patient and provided with an wherein said sound reducing device is composed of a proximal (3a) membrane and a distal (3b) membrane, wherein the distal (3b) membrane is more elastic than the proximal (3a) membrane, which membranes are in contact with each other and close the opening of the bag, said proximal membrane (3a) facing the orifice and said distal membrane (3b) facing the lumen of the bag, wherein the proximal (3a) and distal (3b) membranes are provided with one or more apertures, wherein any aperture in the proximal membrane (3a) is misaligned with any aperture in the distal membrane (3b), whereby passage of waste materials through the opening is blocked until a pressure gradient is established over the proximal (3a) and distal (3b) membrane, which forces the distal membrane (3b) towards the lumen of the bag (2) thereby establishing passage through the apertures of the proximal (3a) and distal (3b) membrane.

In a preferred embodiment the membranes are disc formed and the opening is circular. The membranes (3a, 3b) are preferably glued to said opening, but welding and other ways of attaching the membranes are also envisaged.

The membranes (3a, 3b) are preferably elastic, especially the distal (3b) membrane is preferably elastic in order to expand in the direction of the bag lumen, when a certain pressure is established by flatus gases exiting the stoma. The proximal membrane (3a) does not have to be particularly elastic. The membranes may be based on materials selected from the group consisting of: silicone, polyethylene, polyethylene terephthalate, polypropylene, and PVC.

The proximal (3a) membrane is preferably provided with one or more apertures in the peripheral part of the membrane whereas the distal (3b) membrane is provided with one or more apertures in the central part of the membrane. In a particularly preferred embodiment of the present invention the proximal (3a) membrane is provided with three apertures and the distal (3b) membrane is provided with one aperture.

The area of the apertures in the proximal (3a) membrane normally constitutes 10-40% of the total area of the proximal (3a) membrane, and the area of the apertures in the distal (3b) membrane normally constitutes 5-30% of the total area of the distal (3b) membrane. However, in a preferred embodiment the area of the apertures in the proximal (3a) membrane constitutes 15-25% of the total area of the proximal (3a) membrane, whereas the area of the apertures in the distal (3b) membrane constitutes 10-20% of the total area of the distal (3b) membrane.

In a preferred embodiment the membranes (3a, 3b) protrude in a semi-spherical configuration into the lumen of the ostomy bag. In this way the tension on the distal membrane (3b) is higher than the tension exerted on the proximal membrane (3a), which is important for the correct establishment of passage (and subsequent closing) via the apertures; the tension difference eliminate undesired vibrations.

DETAILED DESCRIPTION OF THE INVENTION

Figure 1:
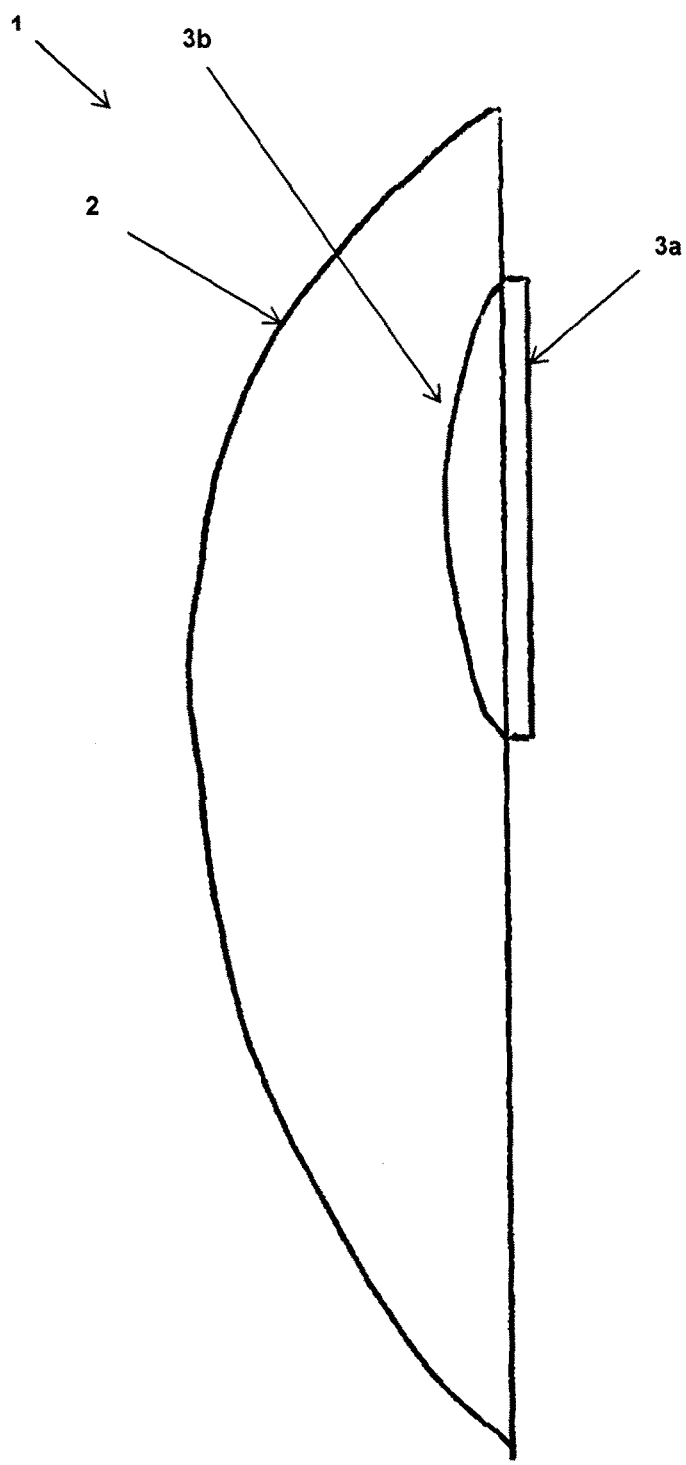
FIG. 1 shows a view of the ostomy bag assembly of the present invention, wherein the membranes extend in a semi-spherical manner towards the lumen of the bag.

In accordance with the present invention the term "stoma" shall be understood to refer to any surgically constructed opening, which connects a portion of the body cavity to the outside environment. Typically, stomas are provided in the abdominal wall of an ostomate that has undergone some form of ostomy procedure where a stoma is created (so as to permit the passage of waste or discharge there through).

It will be understood by a person skilled in the relevant art that the term "ostomy procedure" refers to any surgical procedure that creates a stoma for the discharge of body waste. An ostomy procedure may be performed as a result of or due to a number of conditions. It will be understood that there are different types of ostomies performed depending on how much and what part of the intestine is removed. For example, a colostomy can be performed when a portion of the colon (large intestine) is brought to the surface of the abdominal wall to allow stool to be eliminated. An ileostomy can be performed when an opening is created in the small intestine to bypass the colon for stool elimination. The end of the ileum, which is the lowest part of the small intestine, is brought through the abdominal wall to form a stoma and is called an ileostomy. An ileostomy might be performed due to ulcerative colitis, Crohn's disease, or familial polyposis.

It will be further understood by a person skilled in the relevant art that the term "ostomy bag" refers to an ostomy pouching system or apparatus that provides a means for the collection of waste from the biological system (such as; colon, ileum, jejunum) diverted as a result of the ostomy procedure. Ostomy devices or bags are also sometimes referred to as "assemblies". Such ostomy devices or assemblies are well known in the art and generally comprise a mounting plate (face plate), also referred to as a wafer or a flange, which is attached to the skin with an adhesive in an air- or water-tight seal, and a collection pouch that may be attached mechanically to the mounting flange. The flange is affixed to the skin and has an opening that is in communication with the stoma. The collection pouch of the ostomy device also has an opening that operates such that when the pouch is connected (e.g. connected so as to create an air- and water-tight seal between the pouch and the mounting plate) to the mounting plate, the material (e.g. solid, liquid and gas waste material) that is outputted or released from the stoma is collected in the collection pouch. In operation, therefore, the ostomy device allows the stoma to drain into the collection pouch, while protecting the surrounding skin from contamination. It will be understood that a number of different ostomy device designs are well known to those skilled in the relevant art, including, one- and two-piece designs. Two-piece designs allow the changing and use of multiple pouches while retaining the wafer/baseplate for several days. The selection of systems varies greatly between individuals and is often based on personal preference and lifestyle. In operation, it will be understood to a person skilled in the relevant art that ostomy devices allow the ostomate to lead an active lifestyle that can include all forms of sports and recreation. The embodiments of the present invention are not, therefore, restricted to specific designs or configurations of ostomy devices. The embodiments of the present invention can be used with any ostomy device having a structure substantively similar to the structure noted above. It will be understood that the disc and cushion can be either inside or outside of the ostomy pouch adjacent to the stoma.

It will be understood by a person skilled in the relevant art that the term "ostomate" as used herein refers to individuals who have undergone an ostomy procedure and wear an ostomy device. The present invention is directed to providing ostomates (e.g. persons having undergone an ostomy procedure and wearing an ostomy device) with an improved psychological adjustment, privacy, security and ability to pursue a variety of physical activities through increased confidence, comfort and safety. The embodiments of the present invention may facilitate daily life for the ostomates and may allow ostomates to pursue active, fulfilling and productive lives without any significant limitations of activity.

The present invention provides a means of attenuation (e.g. reduction or elimination) of the sound made from the emission of waste material (e.g., flatus gasses) through the stoma or stomal aperture thereby enabling user confidence in social environments. An aspect of the present invention is directed to achieving such sound attenuation by shifting the pressure gradient, which is normally over the stoma toward the noise attenuating device of the present invention.

Thus, in general, the present invention relates to devices for the attenuation of noise emanating from a surgically created abdominal stoma, particularly stomas formed from ostomies such as colonostomies and ileostomies. The present invention provides a sound reducing device that is relative small, compact and low profile, as compared to prior systems. Further, the sound reducing device reduces the amount of irritation and discomfort an individual must endure, particularly in public settings. Still further, the sound reducing device gives the user a higher level of confidence in public settings as the device eliminates or drastically reduces stoma noises and is discrete.

The present invention solves the problems with stoma noise by providing a sound reducing means, which significantly reduces the vibrations produced in the stoma when flatus gases (and other bodily waste) escape the body. The problem has been solved by a membrane sandwich (composed of two membranes in immediate contact and with misaligned apertures) that blocks the passage from the stoma to the lumen of the ostomy bag unless the membranes are expanded due to the pressure difference established when flatus gases escape the stoma. As explained below the flatus gases force the membranes (and in particular the membrane closest to the bag) to expand, whereby there is created a passage through the apertures.

Figure 2:
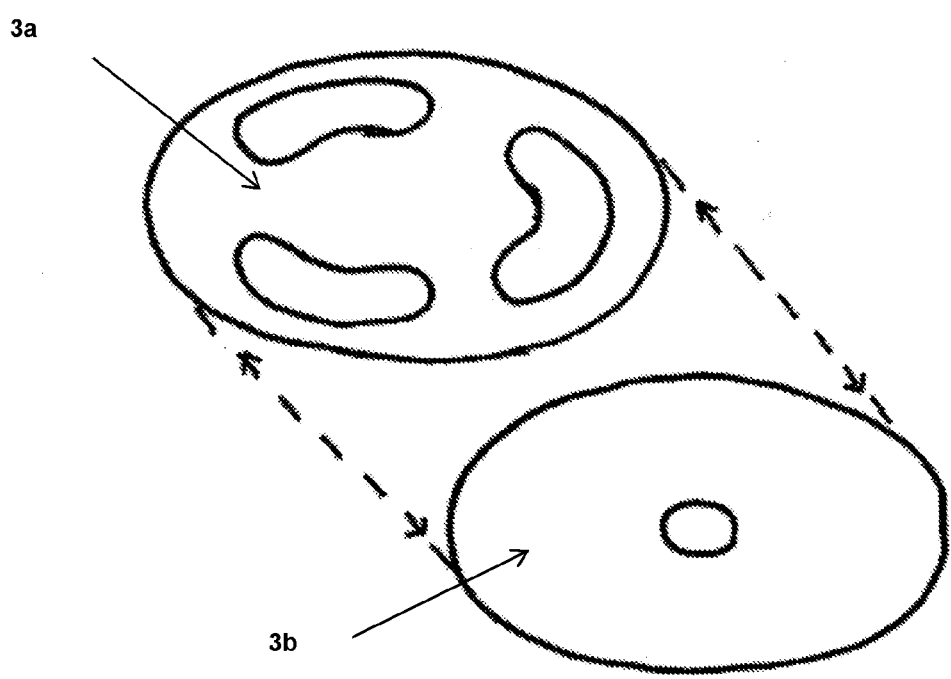
FIG. 2 shows a view of the proximal (3a) membrane and a distal (3b) membrane when separated from each other.

In a preferred embodiment of the present invention the ostomy bag (2) has an opening in which the disc formed membranes (3a, 3b) have been firmly attached to the edge of the opening. As appears from FIG. 1 the sandwiched membranes (3a, 3b) extend in a semi-spherical manner towards the lumen of the ostomy bag (2). This means that the pressurized air enters the apertures of the proximal (3a) membrane and forces the distal (3b) membrane to expand and thus loose contact with the proximal (3a) membrane. Hereby a passage (or channel) is established through the apertures of the proximal (3a) and distal (3b) membrane. FIG. 2 shows the disc formed membranes (3a, 3b) when separated from each other.

The invention claimed is:

1. An ostomy bag assembly with sound reducing means comprising:
a bag for receiving bodily waste materials through an opening;
a sound reducing device positioned in the opening of the bag; and
a flange for securing the assembly to the body of a patient and provided with an orifice to enable bodily waste to be received in the opening of the bag;
wherein said sound reducing device is composed of a proximal membrane and a distal membrane, wherein the distal membrane is preferably more elastic than the proximal membrane, which membranes are in contact with each other and close the opening of the bag, said proximal membrane facing the orifice and said distal membrane facing the lumen of the bag, wherein the proximal and distal membranes are provided with one or more apertures, wherein any aperture in the proximal membrane is misaligned with any aperture in the distal membrane, whereby passage of waste materials through the opening is blocked until a pressure gradient is established over the proximal and distal membrane, which forces the distal membrane towards the lumen of the bag thereby establishing passage through the apertures of the proximal and distal membrane.

2. The ostomy bag assembly of claim 1, wherein the membranes are disc formed and the opening is circular.

3. The ostomy bag assembly of claim 1, wherein said membranes are glued to said opening or one end of a tube is attached the opening, whereby the membranes are glued to the other end of the tube.

4. The ostomy bag assembly claim 1, wherein the membranes are based on materials selected from the group consisting of: silicone, polyethylene, polyethylene terephthalate, polypropylene, and PVC.

5. The ostomy bag assembly claim 1, wherein the proximal membrane is provided with one or more apertures in the peripheral part of the membrane and the distal membrane is provided with one or more apertures in the central part of the membrane.

6. The ostomy bag assembly of claim 5, wherein the proximal membrane is provided with three apertures and the distal membrane is provided with one aperture.

7. The ostomy bag assembly of claim 1, wherein the area of the apertures in the proximal membrane constitutes 10-40% of the total area of the proximal membrane, and the area of the apertures in the distal membrane constitutes 5-30% of the total area of the distal membrane.

8. The ostomy bag assembly of claim 7, wherein the area of the apertures in the proximal membrane constitutes 15-25% of the total area of the proximal membrane, and the area of the apertures in the distal membrane constitutes 10-20% of the total area of the distal membrane.

9. The ostomy bag assembly claim 1, wherein the membranes protrude in a semi-spherical configuration into the lumen of the ostomy bag.

10. The ostomy bag assembly of claim 1, wherein the distal membrane is more elastic than the proximal membrane.

* * * * *